(12) United States Patent
Fischer

(10) Patent No.: US 6,673,027 B2
(45) Date of Patent: Jan. 6, 2004

(54) POSTURE MEASUREMENT AND FEEDBACK INSTRUMENT FOR SEATED OCCUPATIONS

(76) Inventor: Peter Fischer, Brombergstr. 16, D71083, Herrenberg (DE)

( * ) Notice: Subject to any disclaimer, the term of this patent is extended or adjusted under 35 U.S.C. 154(b) by 22 days.

(21) Appl. No.: 10/162,644

(22) Filed: Jun. 6, 2002

(65) Prior Publication Data

US 2002/0151824 A1 Oct. 17, 2002

Related U.S. Application Data

(63) Continuation-in-part of application No. 09/549,087, filed on Apr. 13, 2000.

(51) Int. Cl.$^7$ ............................ A61B 5/103; A61B 1/117
(52) U.S. Cl. ......................................................... 600/595
(58) Field of Search ................................. 600/595, 300, 600/594, 587; 482/148, 909; 340/573.7; 377/24.2

(56) References Cited

U.S. PATENT DOCUMENTS

| | | | |
|---|---|---|---|
| 4,007,733 A | 2/1977 | Celeste | 128/2 S |
| 4,527,982 A | 7/1985 | Salzman | 434/258 |
| 4,660,829 A | 4/1987 | Whiteneir | 273/29 A |
| 4,665,928 A | 5/1987 | Linial | 128/782 |
| 4,730,625 A | 3/1988 | Fraser | 128/781 |
| 5,012,819 A | 5/1991 | Marras | 128/781 |
| 5,143,088 A | 9/1992 | Marras | 128/781 |
| 5,146,929 A | 9/1992 | Sawhill | 128/781 |
| 5,243,998 A | 9/1993 | Silverman | 128/782 |
| 5,398,697 A | 3/1995 | Spielman | 128/781 |
| 5,400,800 A | 3/1995 | Jain | 128/782 |
| 5,402,107 A | 3/1995 | Rencavage | 340/573 |
| 5,425,378 A | 6/1995 | Swezey | 128/782 |
| 5,433,201 A | 7/1995 | Manthey | 128/660.02 |
| 5,469,861 A | 11/1995 | Piscopo | 128/781 |
| 5,474,083 A | 12/1995 | Church | 128/733 |
| 5,522,401 A | 6/1996 | Brucker | 128/781 |
| 5,533,531 A | 7/1996 | Edwards | 128/782 |

OTHER PUBLICATIONS

"OrthoSon" flyer (1 sheet)=the preferred embodiment of 5,433,201 above.
"Spinex/Spinoscope" flyer (1 sheet)/2 pages).

Primary Examiner—Max F. Hindenburg
Assistant Examiner—Brian Szmal

(57) ABSTRACT

A posture measurement and feedback instrument comprising a signal source and a receiver attached to either half of a hinge. When the hinge is applied to the skin covering the xyphoid process, it pivots in response to slumping, changing the receiver output accordingly. Software is installed on a telecommunication device to store a posture threshold value and generate a feedback signal when the output of a posture sensing means reaches or exceeds the threshold. Software may also be installed on a computer to store posture data and generate posture feedback, while the computer is being used for an unrelated purpose. A person is alerted when sampled posture data meet or exceed a threshold of immobility. When sampled posture data reach or surpass a threshhold of postural dysfunction, exercises suited to reverse that particular dysfunction are selected from a menu.

7 Claims, 3 Drawing Sheets

POSTURE MEASUREMENT AND FEEDBACK INSTRUMENT FOR SEATED OCCUPATIONS

CROSS-REFERENCE TO RELATED APPLICATIONS

Patent Application (continuation-in-part of prior application Ser. No.: 09/549,087 filed on Apr. 13, 2000) of Peter Fischer, US citizen Brombergstr. 16/D71083 Herrenberg/Germany

STATEMENTS REGARDING FEDERALLY SPONSORED RESEARCH OR DEVELOPMENT,

AND REFERENCE TO MICROFICHE APPENDIX

"NOT APPLICABLE"

BACKGROUND OF THE INVENTION

This invention relates to a posture measurement and feedback instrument designed to prevent the slumped or immobile sitting postures that cause dysfunction and pain such as head, neck, and back pain. Especially effected are those who sit for hours every day on a regular basis, which due to the rapid computerization of society is an ever increasing group.

In order to prevent these posture dependent ailments successfully a posture measurement and feedback instrument needs to alert users when they slump or become immobile in an inexpensive, valid, reliable, and user-friendly manner.

Cost

An informal survey of potential consumers revealed that they may be willing to spend about $200 for a personal posture feedback instrument.

Validity

Validity would require that the instrument is able to differentiate healthy from unhealthy posture. The postures identified by the literature to be most harmful for the spine are prolonged episodes of slumped sitting, heavy stoop lifting, and prolonged episodes of immobility regardless of spinal curvature. Therefore a valid posture feedback instrument needs to be able to distinguish upright sitting from slumped sitting, squat lifting from stoop lifting and mobile from immobile posture.

Reliability

Reliability would require that the posture sensor—body interface of the posture feedback instrument be stable enough to prevent measurement error due to displacement. The sensor should in other words not slip or come loose with the regular daily activities of the users. Nor should the posture readings be subject to variability by extraneous forces such as the earth's magnetic field or extremity movement.

User-friendliness

A user-friendly posture feedback instrument requires that (a) it may be applied independently without much ado by a user, (b) one simple calibration of thresholds covers the entire range of postures a user goes through (e.g. alternating between sitting, standing, and lifting), (c) it does not restrict normal activities such as leaning back against a backrest, (d) it may be used inconspicuously, and (e) it is portable.

While the high prevalence of posture dependent back pain has motivated the invention of a number of posture feedback instruments designed to facilitate healthy posture, they have to this point not managed to become a common consumer item, because none of the instruments has to this point succeeded in being cost efficient, valid, reliable and user-friendly. Rather, the prior art suffers from a number of disadvantages:

(a) U.S. Pat. Nos. 5,425,378 (1995), 5,402,107 (1995), and 5,474,083 (1995) only measure body position relative to gravity and in the case of U.S. Pat. No. 5,474,083 (1995) electromyographic activity, both of which are not suited to measure the spinal curvature that differentiates erect from slumped spinal posture.

(b) U.S. Pat. Nos. 5,553,531 (1996), 4,730,625 (1988), 5,522,401 (1996), and 4,007,733 (1977) are integrated in garments, belts, or suspenders, all of which may easily slip relative to the spine or be regarded unfashionable.

(c) U.S. Pat. Nos. 5,143,088 (1992), 5,012,819 (1991), 5,398,697 (1995), and 4,527,982 (1985) are bulky or require to be worn outside the clothing, both of which precludes an inconspicuous application.

(d) Donning and doffing U.S. Pat. Nos. 5,243,998 (1993) requires a user to undress, making it user-unfriendly.

(e) The application of the sensing means of U.S. Pat. Nos. 5,400,800 (1995), 5,146,929 (1992), 5,143,088 (1992) 5,012,819 (1991), and the Spinoscope® (see copy of flyer) to the back of a user requires the help of a second person, making it user-unfriendly. Mounting the sensing means to the back also causes discomfort and displacement of the sensing means when using a back rest thus excluding an application by seated occupations.

(f) U.S. Pat. Nos. 5,400,800 (1995), 5,146,929 (1992), 5,143,088 (1992), 5,012,319 (1991), 4,660,829 (1987), 4,527,982 (1985), 5,398,697 (1995), 4,665,928 (1987), and 5,469,861 (1995) attempt to measure joint motion directly. As opposed to the indirect method of 5,433,201 (1995), where measurement is based on joint movement dependent skin dilation and contraction, the direct method requires an attachment of the sensing means to either of the articulating members of a joint. The sensing means can however only be attached to the skin which displaces relative to the articulating bones with movement. The resulting displacement of the sensing means relative to the joint causes measurement error. Tightening the attachment can only partially solve this problem and causes discomfort and soft tissue dysfunction. Furthermore, the mechanical linkages of U.S. Pat. Nos. 5,400,800 (1995), 5,146,929 (1992), 5,143,088 (1992), 5,012,819 (1991), 4,660,829 (1987), and 4,527,982 (1985) require rotation and sliding of numerous parts relative to one another. Such elaborate hardware arrangement drives up the cost, makes the instrument bulky, and causes friction which in turn reduces measurement sensitivity.

(g) The more elegant solution of U.S. Pat. No. 5,433,201 (1995) avoids all the above-mentioned disadvantages. Rather than trying to obtain a direct measure of joint motion by attaching to either joint member, U.S. Pat. No. 5,433,201 (1995) measures the amount of joint motion dependent skin dilation and contraction as is commonly done with the Schober method of the German physician Paul Schober (1865–1943). The preferred embodiment of U.S. Pat. No. 5,433,201 (1995) with ultrasonic sensing means has been marketed as "OrthoSon" posture trainer (see copy of flyer) at a cost of $600, definitively above what might be paid by an average consumer. Other than cost, other disadvantages of using an ultrasonic transmitter and receiver are that both need to be powered with a separate cable and that the evaluation of the signal is complicated. When the distance between two points on the skin above the spine changes with movement, the travel time of the ultrasound between the transmitter and receiver changes only minutely, requiring a very sensitive microprocessor to measure and subtract subsequent travel times. A Hall signal on the other hand is easily processed and can be fed directly into standard telemetry systems such as the one offered by the company Conrad Electronic. Developing a cost efficient, valid, reliable and user-friendly slump and immobility guard for seated occupations was part of the applicant's doctoral work in physical therapy. This development included the testing of an alternate embodiment of U.S. Pat. No. 5,433,201: the method of measuring joint dependent skin dilation with a simpler and more cost efficient Hall sensor rather than an ultrasonic sensor. Realizing the skin dilation method of U.S. Pat. No. 5,433,201 with Hall sensor technology comprises the application of a magnet to a fist position on the skin and a Hall sensor to a second position on the skin. When choosing a user-friendly application of the magnet and the Hall sensor on the chest rather than the back, the chest's skin with the magnet and Hall sensor on it approximates with slumping and stretches when the spine is straightened. In theory this should change the Hall reading accordingly. Upon testing however, slumping was found to not merely shorten, but to also fold the chest's skin. Accordingly, slumping did not only approximate the magnet and the Hall sensor as the skin shortened and lengthened. Rather, the skin folding also caused a multidimensional rotation of the magnet and the Hall sensor relative to one another. The problem this created was that the approximation of the magnet and the Hall sensor changed the Hall readings one way, while at the same time the associated rotation changed the readings another way. The result was that during a continuous slumping motion, the Hall readings would often begin to reverse midway. Thus, the method of attaching the magnet and the Hall sensor separately as suggested by U.S. Pat. No. 5,433,201 did not allow for valid measures of slumping and had to be abandoned.

Other drawbacks of attaching the magnet and the Hall sensor separately as suggested in U.S. Pat. No. 5,433,201 (1995) were that:
  often the magnet was lost;
  the Hall sensor got no reading when the magnet was applied in too great of a distance from the Hall sensor;
  the earth's magnetic field influenced the Hall readings more than a change in posture when the magnet and the Hall sensor were mounted too far apart;
  slumping caused the magnet and the Hall sensor to collide when they were mounted too close to each other;
  the Hall readings increased or decreased depending on which pole of the magnet was facing the Hall sensor, which caused a misinterpretation of posture data on several occasions when by mistake the magnet was attached with reversed polarity.

(h) None of the prior art instruments above utilize common telecommunication devices such as cellular phones or pagers for posture measurement and feedback. Cellular phones and pagers are well tested mass market products already containing all the means required for posture feedback and posture data recording. Namely, these are a housing, means to attach the housing to the clothing or the dashboard of a user, a user interface, a microprocessor for signal processing and data storage, means for wireless data transmission, and means for generating acoustic, vibratory, and visual feedback. Adding the posture measurement and feedback function to cellular phones and pagers merely requires minor reprogramming of the microprocessor and a connection with a posture sensor, thus providing the cellular phone and pager user group with a very inexpensive, inconspicuous, reliable, and durable posture measurement and feedback option.

(i) None of the prior art instruments above offer computer users the option of using their computer for storage of posture data, threshold calibration, or feedback at the same time as they use another application professionally (as is common for the clock and the help function of computers). This saves the cost for extra posture data storage or feedback means.

(j) None of the prior art instruments alert users when their posture becomes to immobile.

(k) None of the prior art instruments offer a feedback option where a postural dysfunction automatically triggers a display of those exercises best suited to reverse or prevent the harmful effects of that particular postural dysfunction.

OBJECTS AND ADVANTAGES

Accordingly, several objects and advantages of (a) applying the posture signal source and receiver on either half of a hinge, (b) applying the hinge to the skin, where spinal slump creates a horizontal crease across the xyphoid process, (c) using common telecommunication devices such as cellular phones or pagers for posture measurement and feedback, (d) providing the option of allowing computer users to use their regular computer to receive posture feedback or store their posture data while they use their computer for unrelated purposes, (e) providing the option of alerting users when their posture becomes too immobile, and (f) offering a feedback option where a postural dysfunction automatically triggers a display of those exercises best suited to reverse or prevent the harmful effects of that particular postural dysfunction as proposed in the present invention are as follows:

(a) The method of attaching the posture signal source and receiver on either half of a hinge and applying the hinge to a skin area that deforms in response to a defined posture change, translates the resulting multidimensional skin movement into one reliable plane of rotation around the axis of the hinge. Thus, the confounding mixture of linear and rotational motion found with the method of U.S. Pat. No. 5,433,201 (1995) where signal source and receiver are attached directly to the skin, is avoided.

Another advantage of applying the signal source and receiver to a hinge is that it allows for the signal source to rotate around the receiver in steady proximity. As opposed to the method of U.S. Pat. No. 5,433,201 (1995) where the signal source and the receiver approximate and move apart, the fixed mount and steady proximity between signal source and receiver provided by the present invention has a number of significant advantages:

The proximity between signal source and receiver greatly reduces error due to extraneous variables like, in the case of an electromagnetic sensor system, the earth's magnetic field.

The proximity between signal source and receiver also allows for a less intensive signal, which in the preferred embodiment allows for a very small magnet to be used. A small magnet on the other hand reduces cost, weight, bulkiness, and the concern of users who believe strong magnetic fields to be a potential health risk.

The standardized range of signal intensity which results when signal source and receiver are attached to a hinge, allows for the means of signal processing to be standardized accordingly.

Mounting signal source and receiver to the hinge makes the application user-friendly, because users won't have to worry about at which angle and distance they need to be applied.

The application becomes more reproducible and allows for a mathematical conversion of exponential electromagnetic readings into linear degrees of hinge rotation, thus allowing for a close correlation between posture data and the actual posture they represent.

(b) Applying the hinge to the skin, such that the axis of the hinge lies on the crease which appears across the xyphoid process with spinal slumping, was found to be the most effective and lest error susceptive sensor placement for the measurement of slumping as well as stoop lifting. Extensive experimental research showed that this hinge placement is most sensitive to spinal slump and stoop lifting while showing an only insignificant reaction to extraneous movements such as spinal side-bending and rotation, arm movements, respiratory excursions of the ribcage and the abdomen, or alternating between sitting and standing.

(c) Adding a posture measurement and feedback function to common telecommunication devices such as cellular phones or pagers requires only minor modifications and makes inconspicuous and cost efficient posture measurement and feedback available to the users of these devices. Rather than going through the expensive process of building and testing a posture measurement and feedback instrument from scratch, adding a posture measurement and feedback function to cellular phones and pagers allows for a lot of its thoroughly tested and mass produced components to be used. Namely, these are a micro processor, an audio feedback unit, a vibratory feedback unit, means for wireless transmission of data, an user interface, a power supply, and means to attach the instrument to the dashboard or the clothing of a user. Thus adding a posture measurement and feedback function to cellular phones and pagers merely requires a minor reprogramming of their micro processor and connecting a posture sensor. Modified in this manner, cellular phones and pagers provide an utterly inconspicuous method of posture measurement and feedback, because cellular phones and pagers have become so common no one notices them anymore.

(d) With the rapid computerization of society the number of those who sit in front of a computer for hours every day on a regular base is ever increasing. Using the regular computer of these computer users to provide them with posture feedback or to store their posture data (e.g. for posture research) while they use their computer for unrelated purposes, saves the cost for extra posture data storage or feedback means.

Another advantage is that updating personal computer software is a lot easier than reprogramming the microprocessor of a separate posture measurement and feedback instrument. Software updates for the personal computer (even very individual solutions) could for example simply be posted on a web page for download by users. Therefore the preferred embodiment of the present invention reduces the feedback unit carried by the user to the most simple and inexpensive essentials, while the more complex options of posture data storage, posture threshold calibration, and posture feedback are provided via personal computer.

(e) Providing immobility feedback enables users to avoid this harmful immobile posture behavior.

(f) A feedback option where a postural dysfunction automatically triggers a display of those exercises best suited to reverse or prevent the harmful effects of that particular postural dysfunction, allows for a most effective compensation of that particular dysfunction.

BRIEF SUMMARY OF THE INVENTION

In accordance with the present invention a posture measurement and feedback instrument comprises (a) the application of the posture signal source and receiver on either half of a hinge, (b) the application of the hinge to the skin where spinal slump creates a horizontal crease across the xyphoid process, (c) adding a posture measurement and feedback function to common telecommunication devices such as cellular phones and pagers, (d) the method of using the regular computer of computer users as a means of posture measurement and feedback while they use their computer for unrelated purposes, (e) the option of alerting users when their posture becomes too immobile, and (f) the feedback option that a postural dysfunction automatically triggers the display of those exercises best suited to reverse or prevent the harmful effects of that particular postural dysfunction.

Figure 1:
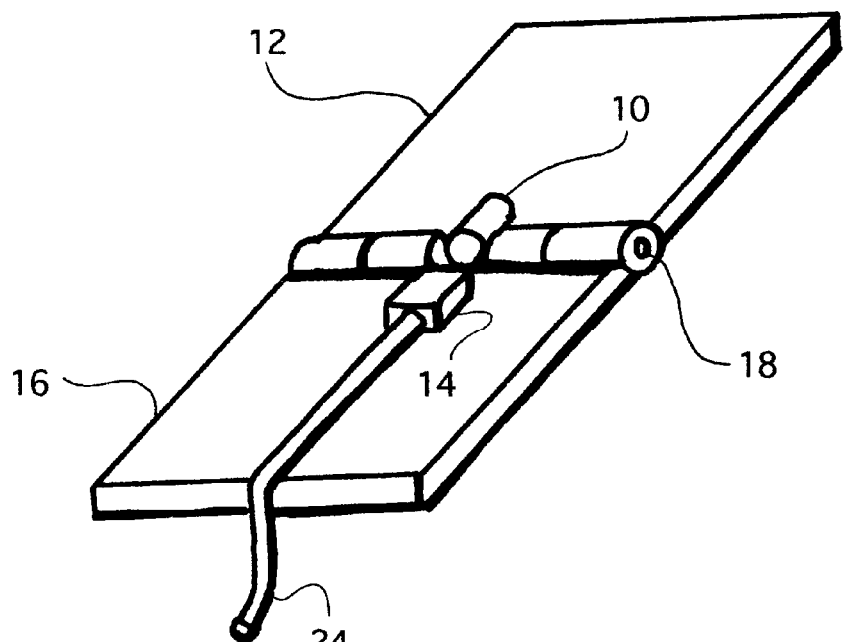
FIG. 1 shows an isometric view of a magnet and a Hall sensor glued to a hinge.

BRIEF DESCRIPTION OF THE REFERENCE NUMERALS OF THE DRAWING 10 magnet
12 first half of a hinge
14 Hall sensor
16 second half of the hinge
18 axis of the hinge
20 first piece of tape
22 second piece of tape
24 cable
26 housing
28 third piece of tape
30 sensor socket
32 data output socket
34 top of the housing
36 switch position for power off and no slump feedback
38 switch position for immediate slump feedback
40 switch position for delayed slump feedback
42 switch position for no mobility feedback 44 switch position for a regular mobility threshold
46 switch position for a extra mobility threshold
48 switch position for no feedback signal
50 switch position for acoustic feedback
52 switch position for loud acoustic feedback
54 switch position for vibration feedback

DETAILED DESCRIPTION OF THE INVENTION

Figure 2:
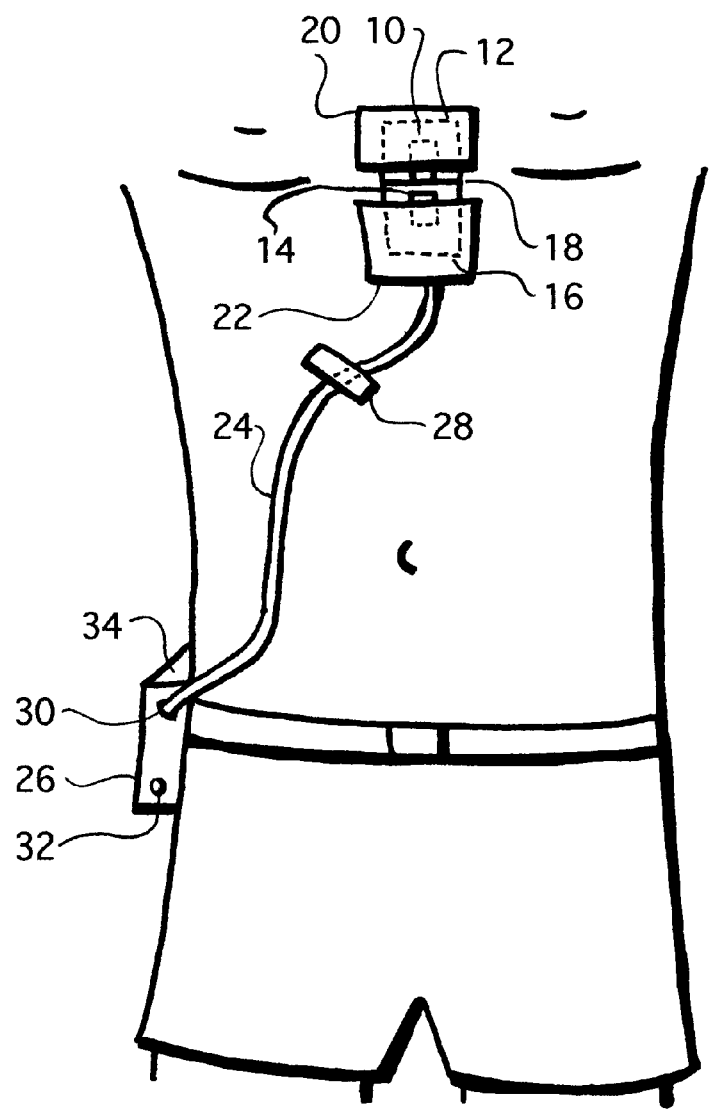
FIG. 2 shows how a cable connects the hinge of FIG. 1 to a housing and how hinge, cable, and housing are applied for slump and mobility feedback.
Figure 3:
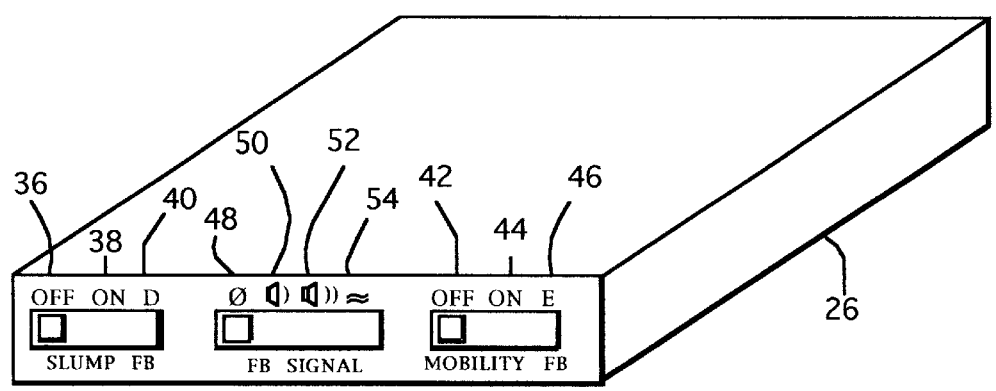
FIG. 3 shows the control panel on top of the housing of the posture measurement and feedback instrument.

A typical embodiment of the posture measurement and feedback instrument of the present invention is illustrated in FIG. 1, where a magnet 10 is glued to a first half of a hinge 12 and a Hall sensor 14 is glued to the second half of the hinge 16. For easier gluing and avoidance of allergic reactions by users, the material of the 38×39 mm hinge used in the preferred embodiment is nylon. So that a particularly small magnet may suffice, a strong Neodym magnet was used in the preferred embodiment. When the hinge hinges around its axis 18, magnet 10 and Hall sensor 14 rotate around each other, causing the output of Hall sensor 14 to change accordingly. FIG. 2 shows how, in order for the hinging to become representative of posture dependent skin deformation, first and second halves 12 and 16 of the hinge are taped to the skin which deforms in response to postural movement with a first and a second piece of tape 20 and 22. A cable 24 through which the output signal from the Hall sensor is transmitted to a portable housing 26 is taped to the skin with a third piece of tape 28 in order to prevent a pull on cable 24 from displacing the hinge. Cable 24 may be easily unplugged from a sensor socket 30 in housing 26 when the clothing is doffed as may become necessary when going to the bathroom. Housing 26 contains a power supply which powers Hall sensor 14 through cable 24, a data output socket 32 for data transmission to a personal computer, a micro processor, an audio feedback unit, a vibratory feedback unit, and an user interface. The user interface of the preferred embodiment is a control panel on the top 34 of housing 26 facing the user. As illustrated in FIG. 3, this control panel is equipped with three switches, allowing a user to adjust the parameters for slump feedback, mobility feedback, and the type of feedback signal. In order to keep the cost of the basic posture measurement and feedback instrument low and handling easy, means for data transmission to a computer were not included in the housing. Rather, data transmission in the preferred embodiment is achieved by plugging the standard telemetry set by Conrad Electronic into data output socket 32 of housing 26. The wireless Conrad Electronic telemetry set for $155 provides not only a real time transmitter and receiver but also the software required for data recording or real time visual feedback on a computer screen. In the $80 version of the Conrad Electronic telemetry set, the real time transmitter and receiver are replaced by a memory module which can later be downloaded into a computer. In order to allow for feedback regarding postural slump, the micro processor within housing 26 stores a threshold value for real time comparison with the subsequent Hall readings, and triggers a signal when the threshold is reached or exceeded. The "slump feedback switch" on the control panel of the preferred embodiment shown in FIG. 3 offers the option of a "power off and no slump feedback position" 36, an "immediate slump feedback position" 38, or a "delayed slump feedback position" 40. In the preferred embodiment the delay is preset at fifteen seconds. The microchip is programmed to store the Hall reading of the posture that is assumed while the "slump feedback switch" is moved from "power off and no slump feedback position" 36 to "immediate slump feedback position" 38 or "delayed slump feedback position" 40 as the slump threshold value. After the research of the applicant showed that none of the seated subjects ever habitually arched their back too much, providing means for the calibration of an extension threshold was waved upon to make the use of the instrument simpler and more cost efficient. Certainly, calibrating a neutral posture or an extension threshold posture could be included as an option in the flexible software of a computer, the data are transmitted to.

In order to allow for immobility feedback, the microprocessor is programmed to sample the incoming posture data with a defined sampling frequency, subtract the values of consecutive samples, and add the absolute values of a defined number of consecutive difference scores. Whenever this sum reaches or surpasses a previously set threshold value, the microprocessor triggers a feedback signal. In the preferred embodiment the sampling frequency for mobility measurement is 1 Hz and the evaluated interval after which mobility feedback may be triggered is fifteen minutes. For the sake of user friendliness, the "mobility feedback switch" on the control panel of the preferred embodiment shown in FIG. 3 offers the choice of either a "no mobility feedback position" 42 or the two experimentally defined and preset thresholds for a "regular degree of mobility position" 44 and an "extra high degree of mobility position" 46.

The options offered by the "feedback signal switch" on the control panel of the preferred embodiment are a "no feedback position" 48, an "acoustic feedback position" 50, a "loud acoustic feedback position" 52, and a "vibration feedback position" 54. In order to differentiate the immobility and slump feedback signals, different rhythms of sound or vibration are used. In the preferred embodiment, immobile posture is signaled at the end of a fifteen minute evaluation interval with a single beep lasting three seconds, while slumped posture is signaled by short intermittent beeps or vibrations that last until the posture is corrected. For reasons of cost efficiency, visual feedback is only provided on the screen of the computers the posture data are transmitted to. The real time feedback on screen is numeric or graphic. In addition, the feedback software for the personal computer is programmed such that after a user-defined interval of slump and immobility measurement, dysfunctional posture will automatically trigger the display of compensatory exercises. When for example the defined immobility and slump thresholds are exceeded, an extension exercise automatically appears on the screen. The duration and number of exercise repetitions suggested is proportional to how slumped or immobile the posture was during the preceding interval of posture measurement.

A second embodiment concerns common telecommunication means such as cellular phones or pagers which already provide a housing, means to attach the housing to a dashboard or the clothing of a user, a micro processor, an audio feedback unit, a vibratory feedback unit, means for wireless data transmission to a computer, an user interface, and a power supply. Adding a posture feedback function to cellular phones and pagers merely requires the steps of connecting an output of a posture sensing means to the microprocessor of the respective telecommunication device, installing microprocessor programming software on a computer, hooking up the computer to the microprocessor of the telecommunication device, and using the microprocessor programming software to program the microprocessor of the telecommunication device such that: (a) an input means of the telecommunication device may be used to set a threshold, and (b) a feedback signal of the telecommunication device is triggered when the output of the posture sensing means reaches or exceeds the set threshold. It is of course most efficient and thus preferred when the posture feedback software is installed by the professionals who program the microprocessor of the respective telecommunication device in the first place. When they first program the microprocessor anyhow, adding the software with posture feedback function is hardly any extra work for them. For example, programming the microcontroller of a cellular phone to elicit a particular signal when the antenna output of the cellular phone signals an incoming telephone call, essentially equals programming the same microcontroller to trigger a different signal when it receives a beyond threshold signal from the output of a posture sensing means. Thus the described addition of a posture feedback function to a telecommunication device during the development stage of its microprocessor by skilled personal is most efficient.

Operation

The manner of using the posture measurement and feedback instrument is as follows:

(a) The housing is attached to the clothing of a user or another suitable location such as the dashboard of a car.

(b) The hinge of FIG. 1 is placed on the chest, such that axis 18 of the hinge lies on the horizontal crease across the xyphoid process which becomes visible with slumping.

(c) In this position, first and second halves 12 and 16 of the hinge are taped to the skin with a first and a second piece of tape 20 and 22, while cable 24 is taped to the skin with third piece of tape 28 in order to prevent a pull on cable 24 from displacing the hinge.

(d) In order to receive slump feedback, the user slumps to the point starting at which he or she want's to receive feedback and moves the "slump feedback switch" from "power off and no slump feedback position" 36 to either "immediate slump feedback position" 38, or "delayed slump feedback position" 40. Immediate slump feedback is advisable when heavy loads are lifted and brief moments of faulty posture can cause back injury. Delayed feedback is preferable with lighter duty, because it allows for mobility beyond the threshold while still preventing harmful episodes of prolonged slumping.

(e) In order to receive feedback when the posture becomes too immobile, the "mobility feedback switch" is moved from "mobility feedback off position" 42 to either "regular mobility threshold position" 44 or "extra mobility threshold position" 46. The latter requires a user to keep moving more and is advisable for users with loose connective tissues and joints which are particularly stressed by immobile posture.

(f) The type of feedback finally, is chosen by setting the "feedback signal switch" to either "no feedback position" 48, "acoustic feedback position" 50, "loud acoustic feedback position" 52, or "vibration feedback position" 54. Vibration feedback is suitable for inconspicuous feedback or when even the loud acoustic feedback signal can't be heard. "No feedback position" 48 is selected when the data are recorded for scientific evaluation or when circumstances demand a slumped or immobile posture.

For visual feedback, the telemetry software of the preferred embodiment offers the choice of several real time animated graphics such as pointers, bar graphs, or line graphs. Because the telemetry set allows for a simultaneous, real time transmission of mobility and slump data on two separate channels, slump and mobility graphics can be simultaneously displayed in separate windows on-screen along with the exercises that are automatically triggered by postural dysfunction. These slump, mobility and exercise windows may be moved to the corner of the screen, while using an unrelated application such as a word processing application. After posture data have been recorded by the telemetry software of the preferred embodiment, they may be replayed or exported into the Excel application for scientific evaluation. This was how the applicant of the present invention tested and re-tested his method again and again until he arrived at the preferred, inexpensive, valid, reliable, and user-friendly embodiment of the present invention.

After setting the "feedback signal switch" and the "mobility feedback switch", they remain in the respective positions unless changed. Therefore subsequent uses of the instrument is as easy as (a) donning the instrument, (b) assuming the slump threshold posture and, (c) switching the instrument on.

Summary, Ramification, and Scope

Accordingly, the reader will see that the posture measurement and feedback instrument of the present invention provides an inexpensive, valid, reliable, and user-friendly method of posture measurement and feedback. Namely, the posture measurement and feedback instrument of the present invention has advantages in that:

(a) Attaching the posture signal source and receiver to either half of a hinge translates the resulting multidimensional skin movement into one reliable plane of rotation around the axis of the hinge and allows for a user-friendly application.

(b) Applying the hinge to the skin, such that the axis of the hinge lies on the crease which appears across the xyphoid process with spinal slumping, allows for the most user-friendly, the most effective, and lest error susceptive sensor placement for the measurement of spinal slump and slump feedback.

(c) Using common telecommunication devices such as cellular phones or pagers for posture measurement and feedback, makes inconspicuous and cost efficient posture measurement and feedback available to the users of these devices.

(d) Allowing computer users to use their regular computer to receive posture feedback or store their posture data while they use their computer for unrelated purposes, provides them with inconspicuous and cost efficient posture measurement and feedback means.

(e) Providing immobility feedback enables users to avoid harmful episodes of immobile posture.

(f) Offering the feedback option of automatically suggesting those exercises best suited to reverse or prevent the harmful effects of a particular postural dysfunction allows for the most effective compensation of that particular postural dysfunction.

Although the description above contains a number of specificities, these should not be construed as limiting the scope of the invention, but as merely providing illustration of the presently preferred embodiment of this invention.

For example, one could:

(a) attach sensor means other than a Hall sensor to the hinge. Optical sensors could for example be used instead;

(b) also measure other postures than slumped posture;

(c) calibrate an extension threshold and a neutral posture position in addition to a slump threshold;

(d) base immobility feedback on parameters other than spinal posture. Immobility feedback could for example be triggered when an electromyographic evaluation shows that the level of muscle activity does not vary sufficiently;

(e) sandwich either half of the hinge between two thin, slightly bigger layers of silicone in order to create soft, comfortable edges and a smooth surface for easy cleaning;

(f) utilize the measurement and feedback instrument of the present invention for other activities like lifting in addition to the sitting it was primarily designed for;

(g) use posture operated animation of a figure in a video game in order to make posture training more fun;

(h) use the output of posture sensing means for posture operated cursor movement on the screen of a computer thus preventing immobile posture habits of users who need to move the cursor for play or work.

Thus the scope of the invention should be determined by the appended claims and their legal equivalents, rather than by the examples given.

I claim:

1. A method for indirectly assessing positions and movements of body parts of a subject comprising the steps of:
   (a) applying a signal source and a receiver to either half of a hinge, causing the received signal to change when said hinge pivots,
   (b) choosing a suitable skin area having properties causing said skin to deform in response to a defined posture change, and
   (c) applying said hinge to said suitable skin area causing said hinge to pivot and change said received signal in response to said defined posture change,
   whereby multidimensional movement of said skin deformation is translated into one reliable plane of rotation around the axis of said hinge.

2. A method for indirectly measuring the degree of slump comprising the steps of:
   (a) choosing the skin area covering the xyphoid process where slumping causes the body to bend while upper and lower extremity movements and breathing have no significant effect, and
   (b) applying to said skin area a sensing means that provides an output in response to said bending.

3. The method of claim 2 wherein said output is compared to a stored threshold value and triggers a feedback signal when said threshold is reached or exceeded.

4. A method for posture feedback to a user of a common telecommunication device comprising the steps of:
   (a) connecting an output of a posture sensing means to said telecommunication device of said user, and
   (b) installing software on said telecommunication device which allows said telecommunication device to store a posture threshold value and generate a feedback signal when said output reaches or exceeds said threshold,
   whereby inconspicuous and cost efficient posture measurement and feedback means become available to the user of said telecommunication device.

5. A method for posture feedback to a computer user and storage of posture data of said computer user comprising the steps of:
   (a) connecting an output of a posture sensing means to the computer of said computer user,
   (b) installing software on said computer which allows said computer to store said output from said posture sensing means and a posture threshold value, and
   (c) generating a feedback signal based on said output while said computer is being used for an unrelated purpose,
   wherein said feedback signal alerts said user if said output reaches or exceeds said stored threshold value.

6. A method for providing immobility feedback comprising the steps of:
   (a) sampling posture data obtained with a posture measurement means with a defined sampling frequency,
   (b) subtracting values of consecutive samples,
   (c) adding the absolute values of said differences between said consecutive samples,
   (d) comparing said sum to a threshold that defines immobility, and
   (e) alerting a person if said sum meets or exceeds said threshold.

7. A method for providing automatic exercise feedback comprising the steps of:
   (a) compiling a menu of exercises suited to reverse or prevent the harmful effects of postural dysfunction,
   (b) collecting posture data with a means of posture measurement,
   (c) comparing said data to a threshold that defines said postural dysfunction, and
   (d) automatically selecting exercises from said menu that are best suited to reverse or prevent said harmful effects of said postural dysfunction when said threshold is reached or surpassed.

* * * * *